United States Patent
Zupkas

[11] Patent Number: 5,735,845
[45] Date of Patent: Apr. 7, 1998

[54] METHOD OF TREATING THE PROSTATE USING CRYOSURGERY

[75] Inventor: Paul F. Zupkas, San Diego, Calif.

[73] Assignee: UROS Corporation, San Diego, Calif.

[21] Appl. No.: 372,953

[22] Filed: Jan. 17, 1995

[51] Int. Cl.$^6$ ................................. A61N 5/02
[52] U.S. Cl. ..................... 606/20; 606/21; 128/898
[58] Field of Search ................... 606/1, 21, 27, 606/20, 22, 192; 128/897–899, 846, 847, 850, 660.01–660.04; 607/96, 113, 104, 105, 107

[56] References Cited

U.S. PATENT DOCUMENTS

| | | |
|---|---|---|
| 1,607,194 | 11/1926 | Gammon et al. . |
| 1,652,954 | 12/1927 | Pierce . |
| 2,204,275 | 6/1940 | Kesling . |
| 3,091,242 | 5/1963 | Johnson, Jr. et al. . |
| 3,827,436 | 8/1974 | Stumpf et al. .......... 607/113 |
| 4,010,795 | 3/1977 | Stenberg . |
| 4,416,281 | 11/1983 | Cooper et al. . |
| 4,605,006 | 8/1986 | Jacques . |
| 4,947,843 | 8/1990 | Wright et al. . |
| 4,955,377 | 9/1990 | Lennox et al. . |
| 5,084,044 | 1/1992 | Quint . |
| 5,195,507 | 3/1993 | Billweis . |
| 5,199,419 | 4/1993 | Remiszewski et al. . |
| 5,222,938 | 6/1993 | Behl . |
| 5,234,004 | 8/1993 | Hascoet et al. .......... 607/113 |
| 5,235,966 | 8/1993 | Jamner . |
| 5,308,327 | 5/1994 | Heaven et al. . |
| 5,309,896 | 5/1994 | Mell et al. . |
| 5,318,586 | 6/1994 | Ereren . |

FOREIGN PATENT DOCUMENTS

9304727   4/1993   WIPO .................. 607/105

Primary Examiner—Robert Nasser
Attorney, Agent, or Firm—Donald E. Stout

[57] ABSTRACT

A surgical instrument comprising a supporting structure and a thermal barrier coupled to the supporting structure. The barrier is sized and adapted for placement between the prostate and rectum during cryosurgical treatment of the prostate. The supporting structure includes a frame movable between an extended position and a retracted position and a handle coupled to the frame. The barrier includes flexible sheet material mounted on the frame and movable with the frame between the extended and retracted positions. The barrier is substantially sonolucent allowing ultrasound visualization of areas beyond the barrier.

20 Claims, 4 Drawing Sheets

METHOD OF TREATING THE PROSTATE USING CRYOSURGERY

BACKGROUND OF THE INVENTION

One known treatment for prostate cancer is to freeze the prostate. This treatment requires not only simple freezing of the prostate but reducing the temperature of the prostate sufficiently so that all cells will die and not be capable of being revived.

To carry out this procedure in a minimally invasive manner, cryosurgical probes are inserted into the prostate and liquid nitrogen is circulated through the probes to obtain the desired freezing effects. To prevent freezing of the urethra, which extends through the prostate, a catheter is placed in the urethra through which warm water flows. Tissue freezes around each cryoprobe in a radial fashion and expands radially outwardly creating an iceball. This iceball continues to grow as long as thermal energy is drawn into the cryoprobe by the circulation of liquid nitrogen through the probe. Transrectal ultrasonography (TRUS) is used to place the cryoprobes in the prostate and monitor growth of the ice ball. This is accomplished by placement of an ultrasound probe in the rectum. At some point the surgeon turns off the flow of liquid nitrogen to the cryoprobes. However, the freezing process continues in the periphery of the iceball for some time after the flow is terminated. Accordingly, the surgeon must use his judgement when to terminate the flow of liquid nitrogen to freeze a defined mass of tissue.

One problem with this procedure is that appropriate freezing of the prostate creates a risk of freezing of adjacent tissue to the extent that it cannot be revived. Unfortunately, TRUS is not capable of distinguishing between tissue that is frozen and capable of being revived and tissue that is frozen and not capable of being revived. The prostate is surrounded by fat, which is a insulator, the bladder which is a large heat sink full of warm fluid and the rectum which rests on the posterior portion of the prostate. It is the rectum which incurs the greatest risk of unacceptable or tissue destroying freezing.

SUMMARY OF THE INVENTION

This invention reduces the likelihood of tissue destruction of the rectum by interposing a thermal barrier between the prostate and the rectum to reduce heat transfer between the prostate and the rectum. This can be accomplished in a minimally invasive manner by utilizing an expandable thermal barrier, inserting the thermal barrier in a collapsed or retracted condition through a small incision in the perineum and then expanding the thermal barrier in a direction laterally of the rectum. If desired, the thermal barrier may also be used like a retractor to separate the prostate from the rectum.

This invention also provides a surgical instrument which includes a supporting structure and the thermal barrier, the latter being coupled to the supporting structure and being sized and adapted for placement between the prostate and rectum during cryosurgical treatment of the prostate. To enable insertion of the barrier in a minimally invasive manner, the supporting structure may include a frame movable between an extended position and a retracted position. The supporting structure may also include a handle coupled to the frame to facilitate positioning and manual manipulation of the frame.

To enable the barrier to be extended or expanded and retracted or collapsed, it preferably includes flexible sheet material mounted on the frame and movable with the frame between the extended and retracted positions. To reduce the likelihood that the thermal barrier will have an unacceptable effect on the ultrasound signals and hence on visualization, the thermal barrier is preferably substantially sonolucent. Because of the sonolucent nature of the thermal barrier, the transmission of an ultrasound signal from the probe in the rectum through the thermal barrier to the prostate enables an appropriate ultrasound image of the prostate to be obtained.

A primary purpose of the thermal barrier is to prevent heat transfer across it, and so the barrier may comprise one or more layers of thermal insulating material. Alternatively, the flexible sheet material of the thermal barrier may have an interior region or chamber for fluid. The fluid may be static, i.e. retained within the barrier as part of the barrier or flow through the barrier. This latter arrangement is preferred, and in this event the flexible sheet material preferably defines a flow passage for fluid. In a preferred construction, the supporting structure and the barrier have a passageway for fluid that enable fluid to be passed through the passageway. When this is done, the temperature of the fluid entering the flow passage may be controlled to achieve the desired thermal barrier effect, and preferably the fluid entering the flow passage is heated, and its temperature can be controlled as desired.

The flow passage through the thermal barrier may define a flow path of various configurations such as a tortuous or winding flow path and a plurality of parallel flow paths. These and certain other configurations have the advantage of providing a defined flow passage which reduces the likelihood of shunting of the circulating fluid directly from the inlet to the outlet and around the area of greatest interest, which is the central region of the thermal barrier. By providing a flow passage that extends through this central region and preferably through a substantial portion of the thermal barrier, there is greater likelihood of achieving the desired thermal barrier effect where it is needed the most.

The thermal barrier can be constructed in different ways to provide the fluid passage for fluid. In a preferred construction, the flexible sheet material includes confronting walls joined together to define a flow passage for fluid.

A preferred way to implement a frame which is movable between extended and retracted positions is to provide a frame which includes first and second lever sections pivotally connected for movement between these positions. The first and second lever sections can be pivoted in various different ways between the extended and retracted positions, and one preferred way is to accomplish this with a handle which includes third and fourth lever sections coupled to the first and second lever sections, respectively. This creates a scissors-type handle-frame construction which is easily maneuverable and permits extending and retracting of the thermal barrier.

If the thermal barrier is to include an interior region for a fluid, then the supporting structure preferably has an inlet passage leading to the interior region and an outlet passage leading from the interior region to enable fluid to be circulated. The inlet and outlet passages extend along, and preferably through, both the handle and the frame. In the case where the handle includes the third and fourth lever sections, the inlet and outlet passages may extend through the third and fourth lever sections, respectively.

When in use, the thermal barrier is positioned between the prostate and the rectum with the barrier extending laterally beyond the rectum on both sides of the rectum. The thermal barrier should have minimum dimensions at least sufficient to cover the prostate and as such, is preferably at least one inch wide and at least two inches in length. In general, the minimum dimensions which allow the thermal barrier to completely cover the prostate and perform its thermal barrier function are most desirable in the interest of minimizing tissue trauma due to the size of the device. In a preferred construction, the thermal barrier has a length of no more than about 3.5 inches and a width of no more than about 3 inches. To obtain a property of sonolucence, the sheet material is preferably a polymeric material having an acoustic impedance similar to tissue, and polyethylene, polypropylene, PVC and polyurethane are examples of polymeric materials which can be provided in appropriate thicknesses to achieve an acceptable level of sonolucence. In addition, the thickness of the sheet material should not be so great as to attenuate the ultrasound signals by an unacceptable amount. For example, if the thickness of the sheet material is half the wavelength of the pulse of ultrasound and the acoustic impedances of the materials defining the interfaces are similar, the sheet material should transmit the ultrasound pulses sufficiently to obtain adequate visualization. To accomplish this, the sheet material is preferably thin and for ultrasound pulses of 2 to 10 Mhz, the impedance matched material is preferably from about 0.075 mm to about 0.360 mm thick.

Another consideration affecting the thickness of the sheet material is the strength of the material to withstand fluid pressure. The fluid pressure may be used, for example, to move the barrier to the extended or expanded position. This may require, for example, a fluid pressure of about 20 to 30 psi. However, if this is not the case, the sheet material need only withstand pressures required to support the circulating fluid and this may be in the range of about 5 psi. Generally, the polymeric materials identified above should be sufficiently strong to withstand any of these pressures if they have a thickness of at least about 0.075 to about 0.150 mm.

The fluid may be either a liquid or a gas. However, if sonolucence is required, the fluid should be a liquid, such as water. Liquids are also preferred because they are generally a better heat transfer medium.

The invention, together with additional features and advantages thereof may best be understood by reference to the following description taken in connection with the accompanying illustrative drawings.

DESCRIPTION OF THE PREFERRED EMBODIMENTS

Figures 1, 2:
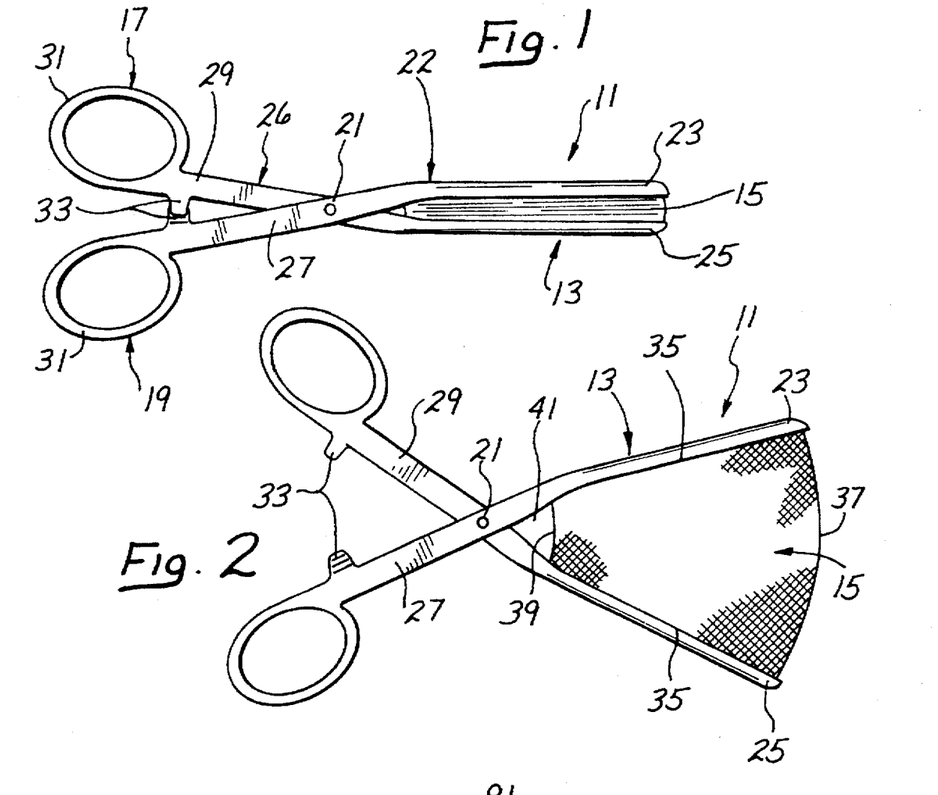
FIG. 1 is a plan view of a surgical instrument constructed in accordance with the teachings of this invention illustrating the frame and thermal barrier in the retracted or collapsed position.
FIG. 2 is a view similar to FIG. 1 illustrating the frame and thermal barrier in the extended or expanded position.

FIGS. 1 and 2 show a surgical instrument 11 which generally includes a supporting structure 13 and a thermal barrier 15. Although the supporting structure 13 can take various different forms, in this embodiment, it includes two arms 17 and 19 pivotally joined intermediate their ends by a pin 21 to form a scissors like construction. With this construction, the supporting structure 13 may be considered as comprising a frame 22 which includes lever sections 23 and 25 of the arms 19 and 17, respectively, pivotally connected by the pin 21 for movement between an extended position shown in FIG. 2 and a retracted position shown in FIG. 1. Also, the supporting structure 13 may be considered as including a handle 26 which, in this embodiment, includes lever sections 27 and 29 of the arms 19 and 17, respectively, coupled to the lever sections 23 and 25, respectively, for pivoting the lever sections 23 and 25 between the extended and retracted positions. In this embodiment, each of the arms 17 and 19 is an integral, unitary member constructed of a suitable rigid polymeric material such as high density polycarbonate or a suitable metal such as a medical grade stainless steel. In this embodiment, the lever sections 27 and 29 terminate proximally in finger rings 31, respectively and each of these lever sections has an inwardly facing tab 33 which are engageable in the retracted position of FIG. 1 to define the retracted position.

The thermal barrier 15 includes flexible sheet material mounted on the lever sections 23 and 25 and movable with the lever sections between the extended and retracted positions. The thermal barrier 15 is substantially sonolucent.

In this embodiment, the thermal barrier 15 has no internal fluid passage, but rather functions as a thermal insulating member. As such, the thermal barrier 15 may be constructed of a suitable flexible polymeric material identified above for the barrier, and if sonolucence is not important have a thickness of, for example, about 3.175 mm.

If the barrier 15 is to be sonolucent, it must be capable of transmitting, when in use, a sufficient percentage of ultrasound signals so as to obtain a useful image with the ultrasound equipment. For example, generally air and metals are not considered sonolucent whereas water is sonolucent. The polymers as discussed above for the barrier are sonolucent if sufficiently thin. Thus, where sonolucence is important, the barrier 15 may need to be thinner, and may be, for example, in the range of from about 0.075 mm to about 0.360 mm in thickness.

The thermal barrier 15 is suitably attached along opposite longitudinal edges 35 to the lever sections 23 and 25. In this embodiment in the extended position, the barrier 15 has a curved distal edge 37 and a shorter curved proximal edge 39, the latter being spaced from the lever sections 23 and 25 over most of its length to define therewith a gap 41.

The thermal barrier 15 is sized and adapted for placement between the prostate 43 (FIG. 6) and the rectum 45 as discussed more fully below. Although the thermal barrier 15 can be of various different dimensions, in this embodiment, its width at the distal edge 37 may be about 3 inches, and the length, i.e. the distance between the edges 37 and 35 is may be about 3.5 inches.

With this construction, the lever sections 27 and 29 along with the finger rings 31 act as a handle to facilitate manipulation of the surgical instrument 11. The lever sections 27 and 29 can be pivoted about the pin 21 to move the thermal barrier 15 between the retracted position of FIG. 1 and the extended position of FIG. 2. The use of the surgical instrument 11 in prostate surgery is described more fully below in connection with FIG. 6.

Figure 3:
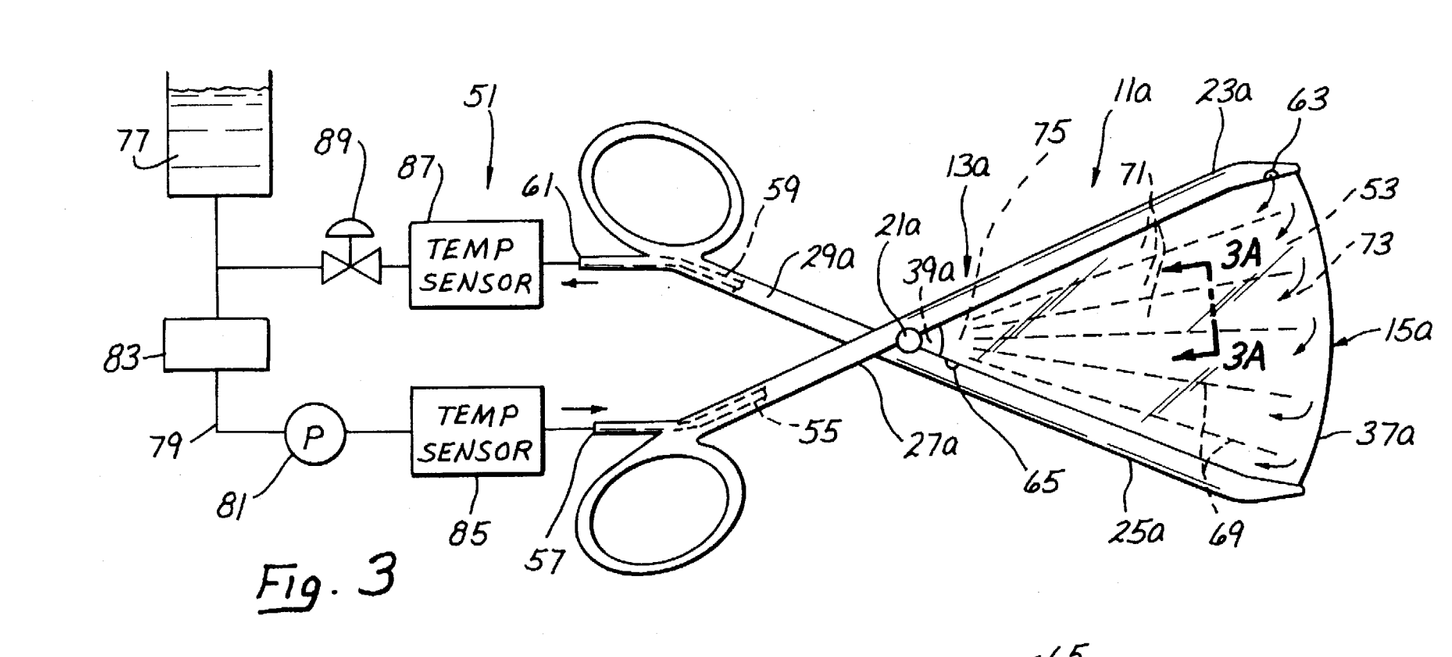
FIG. 3 illustrates a system constructed in accordance with the teachings of this invention and including a second embodiment of surgical instrument.

FIG. 3 shows a system 51 which includes a surgical instrument 11a which is identical to the surgical instrument 11 in all respects not shown or described herein. Portions of the surgical instrument 11a corresponding to portions of the surgical instrument 11 are designated by corresponding reference numerals followed by the letter a.

The primary difference between the surgical instruments 11a and 11 is that the former has an interior region or chamber for a fluid. In this embodiment, the flexible sheet material of the thermal barrier 15a defines a flow passage 53 for a fluid, such as a sterile saline solution. In order to circulate a liquid through the flow passage 53, the supporting structure 13a has an inlet passage 55 leading from an inlet 57 to the flow passage 53 and an outlet passage 59 leading from the flow passage 53 to an outlet 61. Although this can be accomplished in various different ways, in this embodiment, the inlet passage 55 extends through the lever sections 27a and 23a to an opening 63 in the lever section 23a which opens into the flow passage 53 near the distal edge 37a and which forms an inlet to the flow passage. Similarly, the outlet passage 59 extends through the lever sections 29a and 25a to an opening 65 which opens into the flow passage 53 near the proximal edge 39a and which forms an outlet from the flow passage. In this manner, a liquid can be circulated from the inlet 57 through the flow passage 53 to the outlet 61.

Although the flow passage 53 can be of different configurations, preferably it has a configuration which minimizes shunting or short circuiting of the fluid from the opening 63 to the opening 65. In this embodiment, the thermal barrier 15 comprises confronting walls or layers 65 and 67 (FIG. 3A) of flexible polymeric sheet material heat sealed together by flexible partitions 69 of the same material to form a plurality of parallel flow paths 71. As shown in FIG. 3, the partitions 69 do not extend for the full length of the barrier 15a to thereby provide a feeder channel or main 73 along the distal edge 37a and a collection chamber 75 adjacent the proximal edge 39a. Thus, the partitions 69 and the flow paths 71 form a fan-like configuration which extend from the feeder channel 73 to the collection chamber 75, and this tends to assure that fluid flow will occur throughout substantially the full area of the thermal barrier 15 and in particular through a central region of the thermal barrier where obtaining flow is particularly important.

Figure 3A:
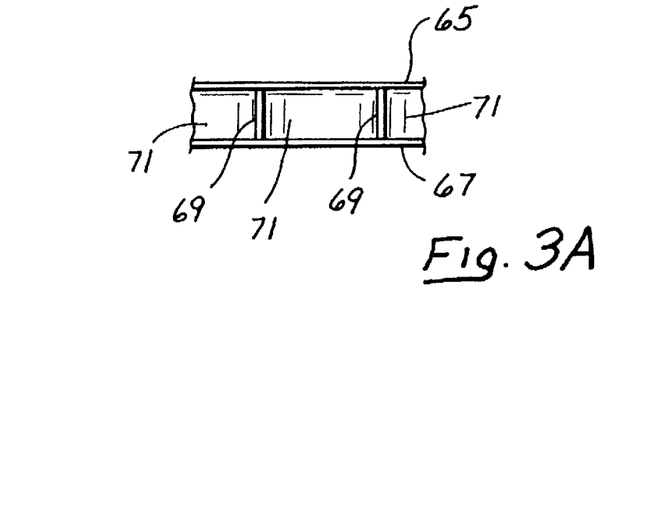
FIG. 3A is an enlarged fragmentary sectional view taken generally along line 3A—3A of FIG. 3.

The cross sectional area of each of the flow paths 71 can be determined in accordance with the results desired. For example, the cross sectional areas of each of the flow paths 71 may be identical or may be varied in order to obtain more or less flow in particular regions of the barrier 15a. Also, the thickness of each of the flow paths 71 may be selected with a view toward the degree of thermal barrier function that is desired to be obtained from the barrier. By way of example, the flow paths 71 may have a width, i.e. spacing between the partitions so as to provide 4 to 7 flow paths in the barrier 15a and a thickness, i.e. the spacing between the confronting walls 65 and 67 of about 0.125 inch. Each of the partitions 69 is preferably as thin as possible and may be, for example, about 0.003 to about 0.005 inch thick. In order to be sonolucent, each of the walls 65 and 67 is preferably between about 0.075 to about 0.360 mm thick. The presence of the two walls 65 and 67 as well as the thin partition 69 is not considered to prevent the barrier 15a from being sonolucent. In this regard, the ultrasound signals are likely to pass through the barrier 15a in a direction which is approximately perpendicular to the walls 65 and 67, in which event the partition 69 would cover only a very small percentage of the area of the barrier 15a in the applicable direction.

The inlet 57 and the outlet 61 can be coupled to a fluid supply circuit in any desired manner. For example, as shown in FIG. 3, the inlet 57 is coupled to a source 77 of a suitable sonolucent liquid such as sterile saline solution by a conduit 79. Sterile saline solution from the source 79 is pumped by a pump 81 through a heater 83, a temperature sensor 85 and the surgical instrument 11 to the outlet 61. The exiting water then passes through or by a temperature sensor 87 and a valve 89 to a location in the conduit 79 between the source 77 and the heater 83. The temperature sensor 85 can be used either manually or automatically to control the heater 83 to provide water at the desired temperature, such as about 37° C., to the surgical instrument 11. The temperature sensor 87 can be used either manually or automatically to control the valve 89 to thereby control the flow rate through the surgical instrument 11 to obtain the desired heating effect within the patient.

Figures 4, 4A:
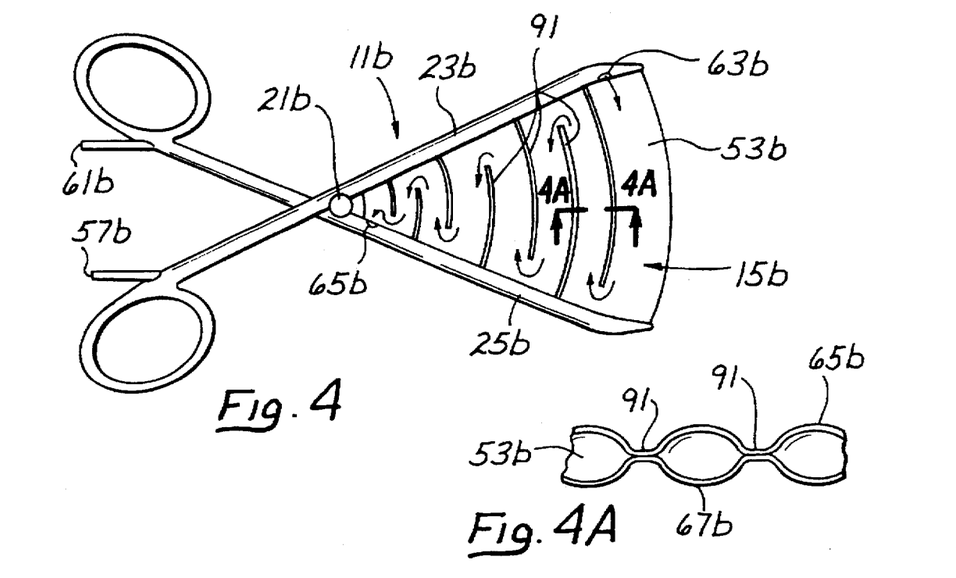
FIG. 4 is an elevational view illustrating a third embodiment of surgical instrument.
FIG. 4A is an enlarged fragmentary sectional view taken generally along line 4A—4A of FIG. 4.

FIGS. 4 and 4A show a surgical instrument 11b which is identical to the surgical instrument 11a in all respects not shown or described herein. Portions of the surgical instrument 11b corresponding to portions of the surgical instrument 11a are designated by corresponding reference numerals followed by the letter "b".

One difference between the surgical instruments 11a and 11b is that the flow passage 53b is a winding, serpentine flow passage rather than the parallel flow paths 71. In addition, the walls 65b and 67b are heat sealed together along seams 91 to define various regions of the flow passage 53 and the partitions 69 of the surgical instrument 11a are eliminated. Of course, the parallel flow paths 71 of FIGS. 3 and 3A can be provided by heat sealing to form seams between the flow paths 71, if desired. The seams 91 extend transversely, but they are sufficiently flexible to permit the barrier 15b to remain sufficiently flexible to be movable between the extended and retracted positions.

Figure 5:
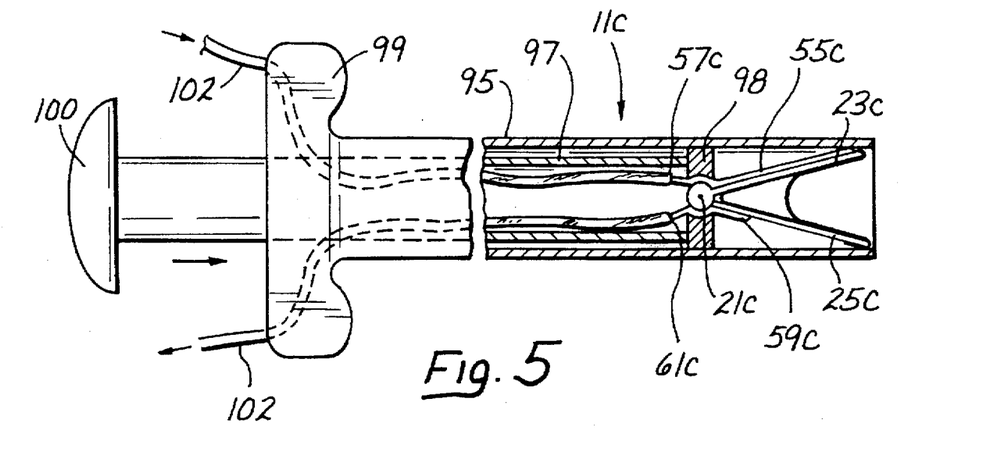
FIG. 5 is a view similar to FIG. 2 illustrating a fourth embodiment of surgical instrument of this invention with the barrier in the retracted position.

FIG. 5 shows a surgical instrument 11c which is identical to the surgical instrument 11a in all respects not shown or described herein. Portions of the instrument 11c corresponding to portions of the instrument 11 are designated by corresponding reference numerals followed by the letter "c".

The instrument 11c includes a frame formed by the lever sections 23c and 25c which are pivotally joined by a pin 21c. Although the thermal barrier 15c may be identical to any of the thermal barriers 15, 15a or 15b, in this embodiment it is identical to the barrier 15a except that it is of slightly different configuration.

The primary difference between the instruments 11a and 11c is that the latter has a handle which comprises a tube 95. In addition a hollow rod 97 is suitably coupled to the proximal ends of the lever sections 23c and 25c and is slidable within the tube 95. A piston 98 is slidable in the tube 95, closes the distal end of the hollow rod 97 and is suitably coupled to the lever sections 23c and 25c adjacent the pin 21c. The handle may also include a disc 99 coupled to the tube 95 adjacent the proximal end of the tube to facilitate manipulation of the instrument 11c. A knob 100 may be provided at the proximal end of the rod 97.

In this embodiment, the barrier 15c has a flow passage and as such, may have a flow passage similar or identical to the flow passages 53 (FIG. 3) or 53b (FIG. 4). The inlet passage 55c and the outlet passage 59c may be provided by additional thicknesses along appropriate lengths of the lever sections 23c and 25c, respectively. The inlet 57c and the outlet 61c are coupled to flexible tubes 102 which extend back through the passage in the hollow rod 97 and out through slotted openings (not shown) in the hollow rod and through openings in the disc 99 for connection to a fluid supply system such the fluid supply system shown in FIG. 3.

Figure 5A:
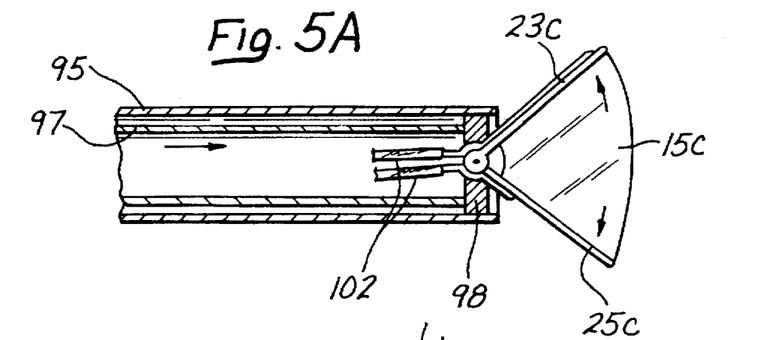
FIG. 5A is a fragmentary sectional view illustrating the embodiment of FIG. 5 with the barrier in the extended position.

The instrument 11c can be used in the same manner as described below for the instrument 11a except that to move the lever sections 23c and 25c and the barrier 15c from the retracted to the extended position, the rod 97 is pushed forwardly (to the right as viewed in FIGS. 5 and 5A) to push the lever sections 23c and 25c and the barrier 15c out of the tube 95 to the position shown in FIG. 5A. Expansion of the barrier 15c, i.e. movement of the barrier to the extended position, is brought about by the fluid pressure within the barrier. However, if the barrier 15c is provided with no flow passage within it such that it is similar to the barrier 15 of FIGS. 1 and 2, then a spring (not shown) may be employed between the lever sections 23c and 25c to resiliently bias the lever sections and the barrier 15 to the extended position when the lever sections are out of the tube 95.

Figure 6:
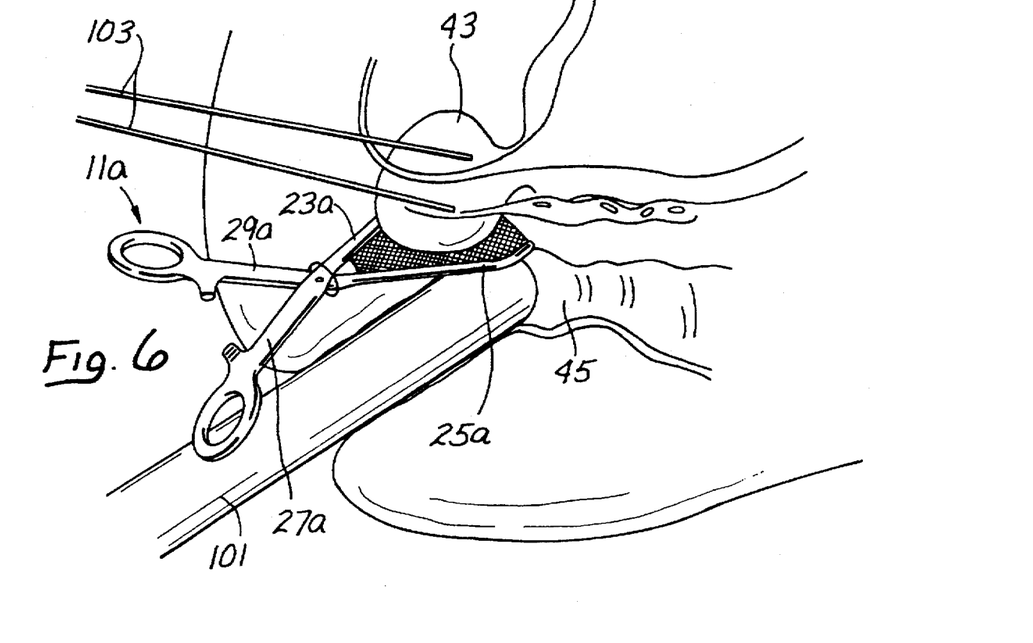
FIG. 6 is a perspective view illustrating use of the surgical instrument of FIG. 3 in carrying out a cryosurgical treatment of the prostate.
Figure 7:
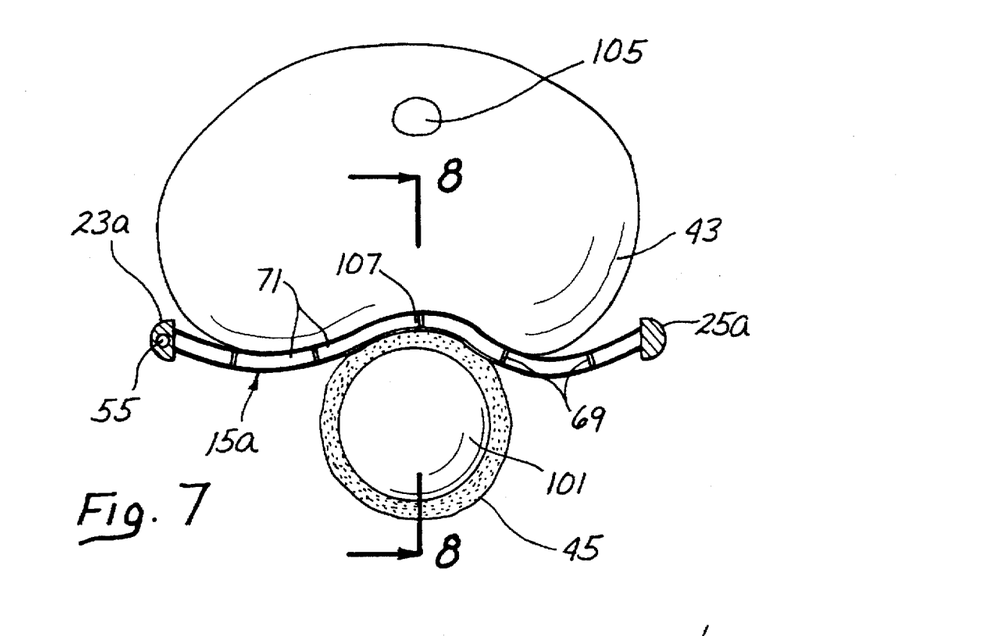
FIG. 7 is a transverse sectional view illustrating use the thermal barrier.
Figure 8:
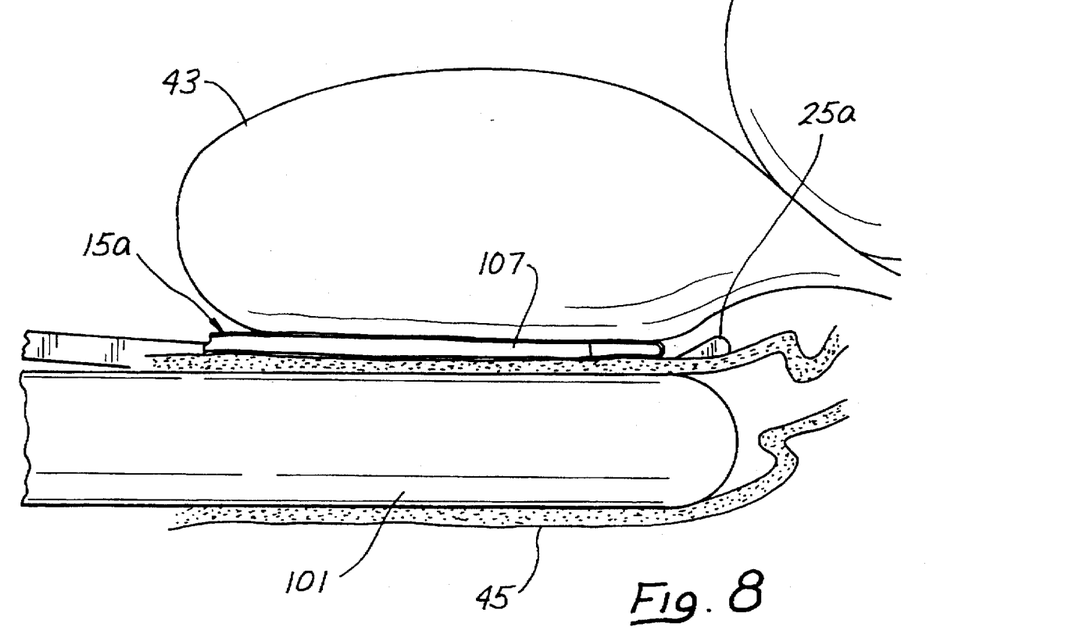
FIG. 8 is a longitudinal sectional view taken generally along line 8—8 of FIG. 7 illustrating use of the thermal barrier.

FIGS. 6–8 illustrate by way of example the use of the surgical instrument 11a in the cryosurgical treatment of the prostate 43. Cryosurgical treatment of the prostate is a known medical procedure and is not described in detail herein. However, generally this known treatment includes inserting an ultrasound probe 101 into the rectum and transmitting ultrasound signals from the probe to the prostate as a plurality of cryoprobes 103 are inserted into the prostate 43. This known treatment also includes placing a catheter (not shown) in the urethra 105 (FIG. 7) and flowing warm water through the catheter to prevent freezing of the urethra during the cryosurgical procedure.

Prior to the present invention, liquid nitrogen was caused to flow through the cryoprobes 103 in a conventional manner and transrectal ultrasonography (TRUS) provided in part by the probe 101 was used to monitor the growth of the ice ball or freezing of the prostate 43. The space between the prostate 43 and the rectum 45 is often between 3 and 5 mm (FIG. 5), and thus there is danger that the freezing of the prostate may result in freezing of the rectum to such an extent that the tissue cannot be revived. Transrectal ultrasonography cannot adequately determine whether or not the rectum is being frozen to an unacceptable extent.

In use of the system 51 of the present invention, the lever sections 23a and 25a are inserted through a small incision in the perineum, and to make the procedure as minimally invasive as possible, this is accomplished with the instrument in the collapsed or retracted position as shown by way of example in FIG. 1. To get the applicable portions of the instrument 11a between the prostate 43 and the rectum 45, it is necessary to separate the tissue between these two organs, and this can be accomplished either by the instrument 11 and/or by a separate retractor (not shown). In the form shown in FIGS. 6–8, it is assumed that the lever sections 23a, 25a, 27a and 29a are sufficiently rigid to enable the instrument to serve as a retractor to separate tissue sufficiently to enable the lever sections 23a and 25a to be placed in the small region between the prostate 43 and the rectum 45 and to then be pivoted to the extended position shown in FIG. 3A by "opening the scissors" or spreading the lever sections 27a and 29a. In this fashion, the thermal barrier is interposed between the prostate and rectum to reduce heat transfer between the prostate and the rectum and to thereby reduce the likelihood of tissue destruction of the rectum. Thus, the thermal barrier is expanded in a direction transverse to the rectum and the barrier extends laterally beyond the rectum on both sides of the rectum as shown in FIG. 7. As shown in FIG. 8, the thermal barrier 15a is long enough to extend longitudinally completely between the prostate 43 and the rectum 45.

It is particularly important that a central region 107 (FIG. 7) of the thermal barrier 15a which is directly between the prostate and the rectum provide a significant barrier to heat transfer between the prostate and the rectum. Thus, by supplying heated water from the source 77 as shown in FIG. 3A through the instrument and the flow paths 71, reasonable assurance is provided that heated water will flow directly through the central region 107. It is apparent that the temperature of the water entering the flow passage 53a can be controlled by the heater 83 and the temperature sensor 85 and that heating of the water is carried out by the heater 83. The pump 81 pumps the heated water through the flow passage 53 along a plurality of parallel flow paths in the case of the instrument 11a of FIG. 3. Because the thermal barrier 15a is sonolucent, ultrasound signals from the probe 101 can be transmitted through the thermal barrier 15a sufficiently to enable an acceptable ultrasound image of the prostate to be obtained.

The other embodiments can be used in a similar way except for the instrument 11 in which no circulating fluid is used. Of course, for the instrument 11b the heated water is pumped through the flow passage 53b along a winding flow path.

Although exemplary embodiments of the invention have been shown and described, many changes, modifications and substitutions may be made by one having ordinary skill in the art without necessarily departing from the spirit and scope of this invention.

I claim:

1. In a method of cryosurgical treatment of the prostate including freezing at least a portion of the prostate with at least one cryosurgical probe, the improvement comprising:
    inserting a surgical instrument having a retracted flexible sheet material between the prostate and rectum; and
    actuating the surgical instrument to extend the flexible sheet material to form a thermal barrier interposed between the prostate and the rectum to reduce heat transfer from the rectum to the prostate and to thereby reduce the likelihood of tissue destruction of the rectum from the cryosurgical treatment.

2. A method as defined in claim 1 wherein the thermal barrier includes a flow passage and including passing a fluid through the flow passage while the thermal barrier is interposed between the prostate and rectum.

3. A method as defined in claim 2 wherein the fluid passage has an inlet and an outlet and the step of passing includes passing the fluid through the inlet, the flow passage and then to the outlet.

4. A method as defined in claim 2 including controlling the temperature of the fluid entering the flow passage.

5. A method as defined in claim 2 including heating the fluid before the fluid enters the flow passage.

6. A method as defined in claim 1 including passing a fluid through the thermal barrier along a tortuous flow path while the thermal barrier is interposed between the prostate and the rectum.

7. A method as defined in claim 1 including passing a fluid through a defined flow passage in the thermal barrier between an inlet to the flow passage and an outlet from the flow passage to reduce the likelihood of shunting the fluid between the inlet and the outlet and with the flow passage lying at least in part between the prostate and the rectum.

8. A method as defined in claim 1 including passing a fluid through a plurality of parallel flow paths within the thermal barrier while the thermal barrier is interposed between the prostate and the rectum.

9. A method as defined in claim 1 wherein the thermal barrier is expandable and the step of inserting includes inserting the thermal barrier between the prostate and the rectum and then expanding the thermal barrier in a direction laterally of the rectum.

10. A method as defined in claim 1 wherein the step of inserting includes positioning the thermal barrier between the prostate and the rectum with the thermal barrier extending laterally beyond the rectum on both sides of the rectum.

11. A method as defined in claim 1 wherein the step of inserting includes separating the prostate from the rectum using the thermal barrier.

12. A method as defined in claim 1 including inserting an ultrasound probe into the rectum and transmitting an ultrasound signal from the probe through the thermal barrier to the prostate whereby an ultrasound image of the prostate can be obtained.

13. In a method of cryosurgical treatment of the prostate including freezing at least a portion of the prostate with at least one cryosurgical probe, the improvement comprising:
    inserting a surgical instrument having a pair of lever sections supporting a retracted flexible sheet material between the prostate and the rectum; and
    actuating the surgical instrument to extend the pair of lever sections such that the flexible sheet material forms a thermal barrier interposed between the prostate and the rectum to reduce the heat transfer from the rectum to the prostate to thereby reduce the likelihood of tissue destruction of the rectum due to the cryosurgical treatment.

14. A method as defined in claim 13 wherein the flexible sheet includes a flow passage and including a step of passing a fluid through the flow passage while the thermal barrier is interposed between the prostate and the rectum.

15. A method as defined in claim 14 wherein the fluid passage has an inlet and an outlet and the step of passing includes passing the fluid through the inlet, the flow passage and then to the outlet.

16. A method as defined in claim 15 wherein the step of passing includes passing a warm sonolucent fluid.

17. A method as defined in claim 14 wherein the pair of lever sections have a pivot point and the step of inserting includes inserting the surgical instrument to substantially the pivot point.

18. A method as defined in claim 14 wherein the surgical instrument has a tubular handle having a slidable hollow rod in attachment with the pair of lever sections and the step of actuating the surgical instrument includes sliding the hollow rod within the handle.

19. In a method of cryosurgical treatment of the prostate including freezing at least a portion of the prostate with at least one cryosurgical probe, the improvement comprising:
    inserting a surgical instrument having a pair of lever sections supporting a retracted sonolucent flexible sheet material between the prostate and the rectum; and
    actuating the surgical instrument to extend the pair of lever sections such that the flexible sheet material forms a thermal barrier interposed between the prostate and the rectum to reduce heat transfer between the prostate and the rectum to thereby reduce the likelihood of tissue destruction of the rectum.

20. A method as defined in claim 19 wherein the flexible sheet includes a flow passage and including passing a warm sonolucent fluid through the flow passage while the thermal barrier is interposed between the prostate and the rectum.

* * * * *

UNITED STATES PATENT AND TRADEMARK OFFICE
CERTIFICATE OF CORRRECTION

PATENT NO. : 5,735,845
DATED : April 7, 1998
INVENTOR(S) : Zupkas

It is certified that error appears in the above-identified patent and that said Letters Patent is hereby corrected as shown below:

On the title page, in item [56] References Cited, insert the following:

U. S. PATENT DOCUMENTS

| EXAMINER INITIAL | PATENT NUMBER | ISSUE DATE | PATENTEE | CLASS | SUBCLASS | FILING DATE IF APPROPRIATE |
|---|---|---|---|---|---|---|
| | 1 9 0 2 0 1 6 | 03/21/33 | L. G. Copeman | | | |
| | 1 9 4 7 6 4 9 | 02/20/34 | G. J. Kadavy | | | |
| | 5 0 3 4 0 0 6 | 07/23/91 | Hosoda et al. | | | |
| | 5 3 5 3 7 8 4 | 10/11/94 | Nady-Mohamed | | | |
| | 5 4 4 9 3 8 0 | 09/12/95 | Chin | | | |
| | | | | | | |

Signed and Sealed this

Thirteenth Day of April, 1999

*Attest:*

Q. TODD DICKINSON

*Attesting Officer*   Acting Commissioner of Patents and Trademarks